US010980829B2

(12) United States Patent
Lee et al.

(10) Patent No.: US 10,980,829 B2
(45) Date of Patent: *Apr. 20, 2021

(54) COMPOSITION FOR DERMAL INJECTION

(71) Applicants: CG Bio Co., Ltd., Seongnam-si (KR); DNCompany, Seoul (KR); Daewoong Pharmaceutical Co., Ltd., Seongnam-si (KR)

(72) Inventors: Ji Sun Lee, Seongnam-si (KR); Su Hyun Jung, Seongnam-si (KR); Hak Su Jang, Gwangju-si (KR); Jung Eun Choo, Seoul (KR); Hye Young Jung, Yongin-si (KR)

(73) Assignees: CG Bio Co., Ltd., Seongnam-si (KR); DNCompany, Seoul (KR); Daewoong Pharmaceutical Co., Ltd., Hwaseong-si (KR)

( * ) Notice: Subject to any disclaimer, the term of this patent is extended or adjusted under 35 U.S.C. 154(b) by 90 days.

This patent is subject to a terminal disclaimer.

(21) Appl. No.: 16/488,939

(22) PCT Filed: Feb. 27, 2018

(86) PCT No.: PCT/KR2018/002401
§ 371 (c)(1),
(2) Date: Aug. 27, 2019

(87) PCT Pub. No.: WO2018/159984
PCT Pub. Date: Sep. 7, 2018

(65) Prior Publication Data
US 2020/0016191 A1  Jan. 16, 2020

(30) Foreign Application Priority Data
Feb. 28, 2017  (KR) ........................ 10-2017-0026489

(51) Int. Cl.
*A61K 31/728* (2006.01)
*A61K 9/00* (2006.01)
*A61K 45/06* (2006.01)

(52) U.S. Cl.
CPC .......... *A61K 31/728* (2013.01); *A61K 9/0019* (2013.01); *A61K 45/06* (2013.01)

(58) Field of Classification Search
None
See application file for complete search history.

(56) References Cited

U.S. PATENT DOCUMENTS 6,214,331 B1  4/2001  Vanderhoff et al.
7,829,118 B1  11/2010  Gravett et al.
8,124,120 B2  2/2012  Sadozi et al.
2012/0258155 A1  10/2012  Wenk et al.
2013/0089579 A1  4/2013  Laeschke
2013/0203856 A1  8/2013  Cho et al.

FOREIGN PATENT DOCUMENTS

| CN | 100441241 | 12/2008 |
| CN | 104771331 | 7/2015 |
| KR | 10-2006-0127897 | 12/2006 |
| KR | 10-2011-0043730 | 4/2011 |
| KR | 10-2012-0006451 | 1/2012 |
| KR | 10-2014-0000206 | 1/2014 |
| KR | 10-1660211 | 9/2016 |
| WO | WO 2018/159984 | 9/2018 |

OTHER PUBLICATIONS

International Search Report and the Written Opinion dated Jun. 4, 2018 From the International Searching Authority Re. Application No. PCT/KR2018/002401 and Its Translation of Search Report Into English. (17 Pages).
Examination Report dated Feb. 5, 2020 From the Australian Government, IP Australia Re. Application No. 2018228301. (9 Pages).
Chun et al. "Effect of Molecular Weight of Hyaluronic Acid (HA) on Viscoelasticity and Particle Texturing Feel of HA Dermal Biphasic Fillers", Biomaterials Research, 20(24), pp. 1-7, Sep. 2016.
Wallace et al. "Injectable Cross-linked Collagen with Improved Flow Properties", Journal of Biomedical Materials Research, 23(8): 931-945, Aug. 1989.
Rejection Decision dated Sep. 27, 2019 From the Intellectual Property Office of Taiwan R.O.C. Re. Application No. 107196877 and Its Translation Into English. (10 Pages).
Supplementary Partial European Search Report and the Provisional Opinion dated Dec. 3, 2020 From the European Patent Office Re. Application No. 18761255.1. ( 10 Pages).
Draelos "The Effect of a Combination of Recombinant EOF Cos Serum and a Crosslinked Hyaluronic Acid Serum as Appearance of Aging Skin", Journal of Drugs in Dermatology: 15(6): 738-741, Jun. 1, 2016, Abstract.
Stocks et al. Rheological Evaluation of the Physical Properties of Hyaluronic Acid Dermal Fillers, Journal of Drugs in Dermatology 10(9): 974-980, Sep. 2011.
Tezel et al. "The Science of Hyaluronic Acid Dermal Fillers", Journal of Cosmetic and Laser Therapy, 10(1): 35-42, 2008.

*Primary Examiner* — Layla D Berry

(57)  ABSTRACT

The present invention relates to a composition for dermal injection which includes two or more types of cross-linked hyaluronic acid particles having different particle diameters and non-cross-linked hyaluronic acid. The composition for dermal injection according to the present invention satisfies viscosity, extrusion force, and viscoelasticity conditions for dermal injection, and an extrusion force deviation is low so that the user does not feel fatigue when the composition is injected into the dermal thereof. Also, the composition is excellent in viscoelasticity and tissue restoring ability, is maintained for a long period of time, allows rapid recovery because an initial swelling degree is low, and also is excellent in safety and stability in the body.

13 Claims, No Drawings

COMPOSITION FOR DERMAL INJECTION

RELATED APPLICATIONS

This application is a National Phase of PCT Patent Application No. PCT/KR2018/002401 having International filing date of Feb. 27, 2018, which claims the benefit of priority of Korean Patent Application No. 10-2017-0026489 filed on Feb. 28, 2017. The contents of the above applications are all incorporated by reference as if fully set forth herein in their entirety.

FIELD AND BACKGROUND OF THE INVENTION

The present invention relates to a composition for dermal injection.

Hyaluronic acid, as a gel type product having transparency and viscosity, is a biodegradable and highly hydrophilic substance, and plays an important role in maintaining moisture in the dermal, dermal volume, and dermal elasticity because it attracts 214 water molecules per one molecule thereof. Thus, a filler containing hyaluronic acid as an ingredient has been used for restoration of facial dermal elasticity, subtle improvement of a contour, reduction of facial wrinkles, and general cosmetic facial contouring procedures.

However, since natural hyaluronic acid has a half-life of only 1 to 2 days, the hyaluronic acid used in the filler is made in a cross-linking state to be maintained in the dermal for a long period of time. Here, the crosslinking results in preventing the degradation of hyaluronic acid caused by hyaluronidases and increasing viscosity to form volume (Song, Yi-Seop et al., Korean Journal of Dermatology 2014; 52(2):100-105).

Hyaluronic acid fillers currently available on the market are in the monophasic or biphasic form. A monophasic filler is composed of a homogeneous gel so that it has high viscosity, is smoothly injected, and is useful for forming a delicate shape. A biphasic filler is made in the form of a particle by filtering a gel using a sieve so that it has high elasticity, and thus it is possible to maintain shape and increase volume.

Meanwhile, research on the development of a filler having ideal in vivo characteristics and surgical usefulness is continuing. However, a hyaluronic acid filler having excellent in vivo stability has high gel hardness and high viscosity so that it may be difficult to inject the filler through a fine gauge needle. Also, a hyaluronic acid filler capable of being easily injected through a fine gauge needle may have low in vivo stability. Accordingly, hyaluronic acid fillers excellent in both viscosity and elasticity are required.

SUMMARY OF THE INVENTION

The present invention is directed to providing a composition for dermal injection which includes two or more types of cross-linked hyaluronic acid particles having different particle diameters and non-cross-linked hyaluronic acid.

The present invention provides a composition for dermal injection which includes first cross-linked hyaluronic acid, second cross-linked hyaluronic acid having a different particle diameter from the first cross-linked hyaluronic acid, and non-cross-linked hyaluronic acid, wherein the first cross-linked hyaluronic acid particles and the second cross-linked hyaluronic acid particles are included in a weight ratio of 1:0.5 or more to less than 2.5, and the first cross-linked hyaluronic acid particles and the non-cross-linked hyaluronic acid are included in a weight ratio of 1:0.1 or more to 1.2 or less.

DESCRIPTION OF SPECIFIC EMBODIMENTS OF THE INVENTION

The present invention relates to a composition for dermal injection which includes first cross-linked hyaluronic acid, second cross-linked hyaluronic acid having a different particle diameter from the first cross-linked hyaluronic acid, and non-cross-linked hyaluronic acid.

Hereinafter, the configurations of the present invention will be described in detail.

In the present invention, numerical values are presented using expressions such as "A or more", "A or less", "more than A" and "less than A", but in the case of numerical values given without such an expression, it is to be understood that the meaning of "A or more" or "A or less" is implied.

In the composition for dermal injection according to the present invention, the first cross-linked hyaluronic acid and the second cross-linked hyaluronic acid may be included in a weight ratio of 1:0.5 or more to less than 2.5, specifically 1:0.5 or more to less than 1.5.

In addition, the first cross-linked hyaluronic acid particles and the non-cross-linked hyaluronic acid may be included in a weight ratio of 1:0.1 or more to 1.2 or less, specifically 1:0.1 or more to less than 0.5.

Within the above ranges, properties required for the composition for dermal injection, such as viscosity, extrusion force, viscoelasticity, and the like, may be achieved.

Hyaluronic acid is a linear polymer including $\beta$-D-N-acetylglucosamine and $\beta$-D-glucuronic acid alternately bonded to each other, and may be interpreted as including all of hyaluronic acid itself, a salt thereof, and a combination thereof in the present invention. The hyaluronic acid may have a molecular weight of 100,000 to 5,000,000 Da or 1,000,000 to 1,500,000 Da, but the present invention is not limited thereto. Examples of the salt of hyaluronic acid include inorganic salts such as sodium hyaluronate, potassium hyaluronate, calcium hyaluronate, magnesium hyaluronate, zinc hyaluronate, cobalt hyaluronate, and the like and organic salts such as tetrabutylammonium hyaluronate and the like. In the present invention, as the hyaluronic acid, hyaluronic acid itself and a salt thereof may be used alone or in combination of two or more. The hyaluronic acid or the salt thereof may be isolated from a microorganism, synthesized, or commercially available, but the present invention is not limited thereto. For example, the hyaluronic acid may be isolated from *Streptococcus* sp. (*Streptococcus equi* or *Streptococcus zooepidemicus*) and purified.

In the present invention, the cross-linked hyaluronic acid particles may be used in the same sense as hydrated cross-linked hyaluronic acid particles. For example, it may mean that hyaluronic acid has been subjected to a crosslinking reaction through a covalent bond using a hydroxyl group. The moisture content or crosslinking ratio of hyaluronic acid may be adjusted through a common method used in the related art, and may be, for example, 10 to 20 mol % or 10 to 15 mol %.

The hyaluronic acid particles may be crosslinked by a crosslinking agent. The crosslinking agent may be, but is not limited to, ethylene glycol diglycidyl ether (EGDGE), 1,4-butanediol diglycidyl ether (BDDE), 1,6-hexanediol diglycidyl ether, propylene glycol diglycidyl ether, polypropylene glycol diglycidyl ether, diglycerol polyglycidyl ether, 1-ethyl-3(3-dimethylaminopropyl)carbodiimide (EDC), divinyl sulfone (DVS), biscarbodiimide (BCDI), or a combination thereof.

The composition for dermal injection according to the present invention (hereinafter, also referred to as a hyaluronic acid composition) includes two or more types of cross-linked hyaluronic acid particles having different particle diameters.

In the present invention, the first cross-linked hyaluronic acid particle has lower elasticity and higher cohesion than those of the second cross-linked hyaluronic acid particle. For example, at a frequency of 0.01 Hz to 1 Hz, the first cross-linked hyaluronic acid particle may exhibit a G' value of less than 300 Pa and a tan δ value of 0.3 or more.

The tan δ value is a G"/G' value (damping factor), which is a numerical value indicating whether the material is close to a solid or liquid state. Here, G' represents elastic modulus, and G" represents viscous modulus. A tan δ value close to 1 at a frequency of 0.01 to 1 Hz may represent a solution state (low elasticity), and a tan δ value close to 0 may represent an elastic body with high elasticity. Also, it has been reported that as a tan δ value is low and the percentage of elasticity (100×G'/(G'+G")) is high, the duration of a filler is expected to be long.

The first cross-linked hyaluronic acid particles may have an average particle diameter of 10 to 250 μm, specifically, 20 to 200 μm, 50 to 150 μm, 80 to 130 μm, 20 to 100 μm, 100 to 200 μm, 200 to 250 μm, 50 to 100 μm, or 150 to 200 μm.

In the present invention, the average particle diameter is D50 (50% diameter of particle), which means a particle size (volume) of a particle corresponding to the 50 percentile in the particle size distribution curve. Such an average particle diameter is measured using a particle size analyzer (Malvern, MS3000), and water is used as a dispersing solvent. That is, the average particle diameter represents a particle diameter of hydrated cross-linked hyaluronic acid particles.

In the present invention, properties of the second cross-linked hyaluronic acid particle are adjusted according to the size thereof. The second cross-linked hyaluronic acid particle has low viscosity and excellent elasticity compared to those of the first cross-linked hyaluronic acid particle. For example, at a frequency of 0.01 to 1 Hz, the second cross-linked hyaluronic acid particle may exhibit a G' value of 300 Pa or more and a tan δ value of less than 0.3.

The second cross-linked hyaluronic acid may have an average particle diameter of 700 to 1,500 μm or 800 to 1,400 μm, specifically 800 to 1,300 μm, 1,000 to 1,200 μm, 700 to 1,200 μm, 1,200 to 1,500 μm, 700 to 1,000 μm, or 1,000 to 1,500 μm.

The composition for dermal injection according to the present invention includes non-cross-linked hyaluronic acid. The non-cross-linked hyaluronic acid is in the form of a solution and may impart fluidity to the composition for dermal injection.

In the present invention, the first cross-linked hyaluronic acid particles, second cross-linked hyaluronic acid particles, and non-cross-linked hyaluronic acid may be included at 1 to 10 parts by weight with respect to 100 parts by weight of the entire composition.

The composition for dermal injection according to the present invention may further include epidermal growth factor (EGF) in addition to the above-described components. The EGF may be injected into the dermal to stimulate the production of collagen, a fibroblast, and elastin, for example, to increase an effect of tissue restoration.

The EGF may be included at 0.0001 to 0.002 part by weight with respect to 100 parts by weight of the entire composition.

In addition, the composition for dermal injection according to the present invention may further include an anesthetic component. The anesthetic may alleviate pain experienced during injection of the composition.

Such an anesthetic component may be, but is not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, or a combination thereof.

The anesthetic component may be included at 0.1 to 1 part by weight with respect to 100 parts by weight of the composition.

The composition according to the present invention may be used with the addition of other common additives such as an antioxidant, a buffer solution and/or a bacteriostat, a diluent, a dispersant, a surfactant, a binder, a lubricant, or the like as necessary.

The composition for dermal injection according to the present invention may have the following physicochemical properties.

(a) no bubbles in appearance, colorlessness, and transparency;
(b) a pH of 7±1;
(c) a viscosity of 40,000 to 90,000 cP;
(d) an average osmotic pressure of 0.325 osmol/kg±10%;
(e) an extrusion force of 30 N or less;
(f) an elasticity of 75 to 85%; and
(g) a phase angle of 8 to 30°.

The viscosity is the amount that represents the magnitude of internal friction in a fluid, which is the resistance of the fluid to flow. Higher viscosity results in ease of injection and is useful for forming a delicate shape. For example, a monophasic hyaluronic acid filler has high viscosity so that it is smoothly injected and is useful for forming a delicate shape. In the present invention, viscosity may be measured using Brookfield DV3T according to conditions of experimental examples to be described below.

The composition for dermal injection according to the present invention may have a viscosity of 40,000 to 90,000 cP or 60,000 to 80,000 cP.

The extrusion force means extrusion force at an injection rate at which a patient feels comfortable. The expression "a patient feels comfortable" is used to define an injection rate which does not cause injuries or excessive pain in a patient when the composition is injected into the dermal. The term "comfort" used herein encompasses the comfort or ability of a doctor or medical professional to inject the composition as well as the comfort of a patient. In the present invention, extrusion force may be measured using T0-101-161 commercially available from TestOne Co., Ltd. according to conditions of experimental examples to be described below.

Generally, when extrusion force is low, there is no pressure pain during injection of the composition, and injection may be easily controlled.

The composition for dermal injection according to the present invention may have an extrusion force of 30 N or less or 25 N or less.

Viscoelasticity is the property of a material that exhibits both liquid and solid characteristics when a force is applied to the material. In the present invention, viscoelasticity may be measured using a rheometer according to conditions of experimental examples to be described below. Specifically, a force resisting an applied force and a loss of energy in the composition due to the applied force may be measured using a rheometer to determine viscous modulus, elastic modulus, and phase angle.

Elastic modulus (storage modulus; G') means the ratio of strain and stress which an elastic body has within the elastic limit. As the elastic modulus is higher, a composition is rigid and has a greater ability to resist strain.

The composition for dermal injection according to the present invention may have an elastic modulus of 250 to 900 or 500 to 800.

Viscous modulus (loss modulus; G") is a measure of lost energy and pertains to a viscous component of a material.

The composition for dermal injection according to the present invention may have a viscous modulus of 120 to 200 or 130 to 160.

In addition, elasticity may be calculated by the following formula using elastic modulus and viscous modulus values. As the elasticity is higher, tissue restoring ability is excellent, and the duration of a filler is prolonged.

$$\text{Elasticity (\%)} = (100 \times G'/(G'+G''))$$

The composition for dermal injection according to the present invention may have an elasticity of 65 to 90% or 75 to 85%.

In addition, the phase angle is a measure of whether the composition is close to a liquid or solid state. As the phase angle is lower, the composition has solid characteristics, and as the phase angle is higher, the composition has liquid characteristics. In the case of a high phase angle, when deformation occurs due to a force applied from the outside or facial expression, the recovery to the original state is delayed, and the original shape is not maintained. In the case of a low phase angle, the G" value becomes smaller due to an instantaneous response to external deformation factors so that the composition is more like an elastic body than a fluid, and thus the composition does not flow out, and the original shape thereof may be continuously maintained. Thus, it is very important to appropriately maintain elasticity and phase angle values in the composition for dermal injection.

The composition for dermal injection according to the present invention may have a phase angle of 8 to 30° or 10 to 20°.

The composition for dermal injection according to the present invention may be prepared through a method commonly used in the related art.

In addition, the present invention provides a method of restoring tissue, which includes administering the above-described composition for dermal injection to a mammal.

The mammal may be a human.

The tissue restoration refers to temporarily or semi-permanently alleviating body wrinkles or restoring a wrinkle-free state, improving contours, forming volume in the tissue, or regenerating tissues such as in scar healing by injecting the composition. The dermal and tissue refer to those in the face, breast, hip, sexual organ, and other body regions.

In particular, the composition for dermal injection according to the present invention may be selected appropriately according to the degree of wrinkling of a user graded in accordance with the WSRS standard. The WSRS is an acronym for Wrinkle Severity Rating Scale, and classifies the degree of wrinkling of a human into 5 grades (Grades 1 to 5). The Grades 1 to 5 are absence (no of folds), mild (shallow folds), moderate (moderate folds), severe (deep folds), and extreme (very deep folds), respectively. Detailed contents of the WSRS and each grade are described in a document by Am J Clin Dermatol 2004; 5 (1): 49-52 1175-0561, and the present invention can evaluate wrinkles in accordance with the WSRS using a method presented in the document.

Meanwhile, the Ministry of Food and Drug Safety in Korea also classifies the wrinkling degree into mild, moderate, severe, and extreme according to the WSRS through guidelines for approval and review of a dermal cosmetic filler based on a hyaluronic acid raw material issued on December 2017, which proposes to include information on wrinkling degree in describing the purpose of a dermal cosmetic filler.

The composition according to the present invention may be used for moderate folds of Grade 3 or severe folds of Grade 4 in the WSRS.

In addition, a syringe may be filled with the composition for dermal injection to inject the composition into the layers of dermal.

The layers of dermal are classified into the epidermis, dermis, and hypodermis. The composition for dermal injection according to the present invention may be injected into the mid dermis or deep dermis.

Hereinafter, the present invention will be described in more detail with reference to embodiment examples of the present invention. However, the following examples are merely presented to exemplify the present invention, and the content of the present invention is not limited to the following examples. That is, the examples of the present invention serve to complete the disclosure of the present invention, and are provided to make known the full scope of the invention to those of ordinary knowledge and skill in the art to which this invention pertains. This invention should be defined based on the scope of the appended claims.

EXAMPLES

Reference Example. Measurement of Properties (1) Viscosity Measurement

The viscosity was measured according to a viscosity measurement method among the general test methods of the Korean Pharmacopoeia.

Specifically, 500 ul of a composition sample was loaded in a sample cup of a viscometer (DV3T, Brookfield), the sample cup was installed in a CP-52 sample cup, and the rotational speed of the spindle was then set to 2 rpm to measure viscosity.

(2) Extrusion Force Measurement

A compression test was performed using a universal testing machine (T0-101-161, TestOne).

Specifically, a syringe was filled with a composition sample, a 27G ½-inch needle was installed to the syringe, and the syringe was then set in a jig. Afterward, a speed of 50 mm/min and a displacement of 25 mm were set to perform a compression test.

(3) Viscoelasticity Measurement

Rheological properties were measured using a rheometer. Specifically, a sample was placed between parallel plates, and a force resistant to an applied force and a loss of energy were measured while vibrating and rotating the parallel plates to determine the elastic modulus (G'), viscous modulus (G"), and phase angle of the sample.

Conditions for rheometer analysis are as follows.
Frequency: 1 Hz
Temperature: 25° C.
Strain: 5%
Measuring geometry: 20 mm plate
Measuring gap: 0.5 mm
Measuring mode: oscillation mode In addition, elasticity was calculated by the following formula with reference to the measured G' and G" values.

Elasticity (%)=(100×G'/(G'+G"))

Preparation Example. Preparation of Composition for Dermal Injection (1) Preparation of First Cross-Linked Hyaluronic Acid Particles 10 g of sodium hyaluronate, 81 g of purified water, and 9 g of 1 M sodium hydroxide (1 M NaOH) were stirred at 400 rpm under vacuum until the mixture became a transparent gel without granules. Then, 0.5 g of butanediol diglycidyl ether (BDDE) as a crosslinking agent was added thereto and stirred. After the stirring was completed, the container was sealed and a crosslinking reaction was performed under conditions of 80 rpm and 50° C. for 1 hour. Then, a resulting substance was allowed to stand at 27° C. for 16 hours to prepare a gel.

Afterward, the gel thus obtained was input into 30 L of a 0.9× phosphate buffered saline (PBS) solution, and then the PBS solution was exchanged with a new one every 3 hours (3 times/day for 5 days) to eliminate a residual reagent. Then, a resulting substance was passed through a mortar grinder (RS 200 commercially available from Retsch GmbH) for 40 minutes to prepare first cross-linked hyaluronic acid particles.

The first cross-linked hyaluronic acid particles thus prepared had an average particle diameter of about 200 μm.

(2) Preparation of Second Cross-Linked Hyaluronic Acid Particles 20 g of sodium hyaluronate, 117 g of purified water, and 13 g of 1 M NaOH were stirred at 400 rpm under vacuum until the mixture became a transparent gel without granules. Then, 1 g of BDDE as a crosslinking agent was added thereto and stirred. After the stirring was completed, the container was sealed and a crosslinking reaction was performed under conditions of 80 rpm and 50° C. for 1 hour. Then, a resulting substance was allowed to stand at 27° C. for 16 hours to prepare a gel.

Afterward, the gel thus obtained was input into 30 L of a 0.9×PBS solution, and then the PBS solution was exchanged with a new one every 3 hours (3 times/day for 5 days) to eliminate a residual reagent. Then, a resulting substance was passed through a 500 μm standard test sieve to prepare second cross-linked hyaluronic acid particles.

The second cross-linked hyaluronic acid particles thus prepared had an average particle diameter of about 800 to 1,500 μm.

(3) Preparation of Non-Cross-Linked Hyaluronic Acid 2 g of sodium hyaluronate was added to 100 g of purified water and stirred to prepare 2% non-cross-linked hyaluronic acid.

(4) Preparation of Hyaluronic Acid Composition

The first cross-linked hyaluronic acid particles prepared in step (1), the second cross-linked hyaluronic acid particles prepared in step (2), and the non-cross-linked hyaluronic acid were mixed in predetermined contents (g) and content ratios to prepare a hyaluronic acid composition.

Example 1. Evaluation of Properties of Hyaluronic Acid Composition Including Only One or Two of First Cross-Linked Hyaluronic Acid Particle, Second Cross-Linked Hyaluronic Acid Particle, and Non-Cross-Linked Hyaluronic Acid (1) Preparation of Hyaluronic Acid Composition (Comparative Preparation Examples 2-1 to 2-10)

As a comparative example of the composition including all of first cross-linked hyaluronic acid particles, second cross-linked hyaluronic acid particles, and non-cross-linked hyaluronic acid, hyaluronic acid compositions were prepared in the same manner as the preparation example except that the first cross-linked hyaluronic acid particles, second cross-linked hyaluronic acid particles, and non-cross-linked hyaluronic acid were mixed in contents (g) and content ratios as shown in the following Table 1.

TABLE 1

|  | First cross-linked hyaluronic acid particle | | Second cross-linked hyaluronic acid particle | | Non-cross-linked hyaluronic acid | |
| --- | --- | --- | --- | --- | --- | --- |
|  | Content | Content ratio | Content | Content ratio | Content | Content ratio |
| Comparative Preparation Example 2-1 | 10 | 1 | 0 | 0 | 0 | 0 |
| Comparative Preparation Example 2-2 | 10 | 1 | 10 | 1 | 0 | 0 |
| Comparative Preparation Example 2-3 | 10 | 1 | 20 | 2 | 0 | 0 |
| Comparative Preparation Example 2-4 | 10 | 1 | 30 | 3 | 0 | 0 |

TABLE 1-continued

|  | First cross-linked hyaluronic acid particle | | Second cross-linked hyaluronic acid particle | | Non-cross-linked hyaluronic acid | |
| --- | --- | --- | --- | --- | --- | --- |
|  | Content | Content ratio | Content | Content ratio | Content | Content ratio |
| Comparative Preparation Example 2-5 | 10 | 1 | 40 | 4 | 0 | 0 |
| Comparative Preparation Example 2-6 | 10 | 1 | 50 | 5 | 0 | 0 |
| Comparative Preparation Example 2-7 | 0 | 0 | 10 | 1 | 0 | 0 |
| Comparative Preparation Example 2-8 | 0 | 0 | 10 | 1 | 2 | 0.2 |
| Comparative Preparation Example 2-9 | 0 | 0 | 10 | 1 | 4 | 0.4 |
| Comparative Preparation Example 2-10 | 0 | 0 | 10 | 1 | 6 | 0.6 |

(2) Measurement of Properties

Measurement results of viscosity, extrusion force, and viscoelasticity of each of the hyaluronic acid compositions according to Comparative Preparation Examples 2-1 to 2-10 were shown in the following Tables 2 and 3.

TABLE 2

|  | First cross-linked hyaluronic acid particle | Second cross-linked hyaluronic acid particle | Non-cross-linked hyaluronic acid | Viscosity (cP) | Extrusion force (N) |
| --- | --- | --- | --- | --- | --- |
| Comparative Preparation Example 2-1 | 1 | 0 | 0 | 25896 | 31.12 |
| Comparative Preparation Example 2-2 | 1 | 1 | 0 | 87699 | 84.27 |
| Comparative Preparation Example 2-3 | 1 | 2 | 0 | 116539 | 113.36 |
| Comparative Preparation Example 2-4 | 1 | 3 | 0 | 133131 | 137.29 |
| Comparative Preparation Example 2-5 | 1 | 4 | 0 | 149712 | 137.52 |
| Comparative Preparation Example 2-6 | 1 | 5 | 0 | 149194 | 155.88 |
| Comparative Preparation Example 2-7 | 0 | 1 | 0 | 187923 | 136.05 |
| Comparative Preparation Example 2-8 | 0 | 1 | 0.2 | 100510 | 25.89 |
| Comparative Preparation Example 2-9 | 0 | 1 | 0.4 | Unmeasurable | Unmeasurable |
| Comparative Preparation Example 2-10 | 0 | 1 | 0.6 | 90400 | 22.99 |

As shown in Table 2, the compositions including only first cross-linked hyaluronic acid particles or only second cross-linked hyaluronic acid particles exhibited excessively low viscosity or excessively high viscosity to be inappropriate as a filler composition.

In addition, the compositions including first or second cross-linked hyaluronic acid particles and not including non-cross-linked hyaluronic acid exhibited high viscosity and/or high extrusion force, and thus are not appropriate for use as a filler composition. In particular, since non-cross-linked hyaluronic acid plays a role of lubrication, Comparative Preparation Examples 2-1 to 2-7, which do not include non-cross-linked hyaluronic acid, may have a problem in that an extrusion force value significantly fluctuates during injection, there is difficulty in dermal injection, and there is a risk that the user may feel pressure pain.

TABLE 3

|  | First cross-linked hyaluronic acid particle | Second cross-linked hyaluronic acid particle | Non-cross-linked hyaluronic acid | Elasticity | G' | G" | Phase angle |
|---|---|---|---|---|---|---|---|
| Comparative Preparation Example 2-1 | 1 | 0 | 0 | 87.80 | 140.70 | 19.55 | 7.91 |
| Comparative Preparation Example 2-2 | 1 | 1 | 0 | 91.57 | 882.80 | 81.25 | 5.26 |
| Comparative Preparation Example 2-3 | 1 | 2 | 0 | 90.25 | 1087.00 | 117.40 | 5.08 |
| Comparative Preparation Example 2-4 | 1 | 3 | 0 | 93.34 | 1388.00 | 98.98 | 4.08 |
| Comparative Preparation Example 2-5 | 1 | 4 | 0 | 93.36 | 1420.00 | 101.00 | 4.07 |
| Comparative Preparation Example 2-6 | 1 | 5 | 0 | 93.64 | 1689.00 | 114.80 | 3.89 |
| Comparative Preparation Example 2-7 | 0 | 1 | 0 | 95.24 | 2017.00 | 100.90 | 2.86 |
| Comparative Preparation Example 2-8 | 0 | 1 | 0.2 | 87.04 | 1430.00 | 213.00 | 8.47 |
| Comparative Preparation Example 2-9 | 0 | 1 | 0.4 | 78.11 | 880.40 | 246.80 | 15.66 |
| Comparative Preparation Example 2-10 | 0 | 1 | 0.6 | 72.63 | 670.20 | 252.50 | 19.89 |

In addition, as shown in Table 3, the compositions including first and second cross-linked hyaluronic acid particles and not including non-cross-linked hyaluronic acid exhibited low phase angles of 6 or less, and thus are not appropriate as a composition for dermal injection. Also, the compositions according to Comparative Preparation Examples 2-9 and 2-10, which include second cross-linked hyaluronic acid and non-cross-linked hyaluronic acid, exhibited a high phase angle, and thus are not appropriate as a composition for dermal injection.

That is, when all of first cross-linked hyaluronic acid particles, second cross-linked hyaluronic acid particles, and non-cross-linked hyaluronic acid are included, a hyaluronic acid composition which exhibits excellent properties and thus is suitable for dermal injection can be prepared.

Example 2. Evaluation of Properties of Hyaluronic Acid Composition According to Content Ratio of First Cross-Linked Hyaluronic Acid Particles and Second Cross-Linked Hyaluronic Acid Particles (1) Preparation of Hyaluronic Acid Composition (Preparation Examples 1-1 to 1-4 and Comparative Preparation Examples 1-5 to 1-10)

Hyaluronic acid compositions were prepared using first cross-linked hyaluronic acid particles, second cross-linked hyaluronic acid particles, and non-cross-linked hyaluronic acid in contents (g) and content ratios as shown in the following Table 4.

TABLE 4

|  | First cross-linked hyaluronic acid particle | | Second cross-linked hyaluronic acid particle | | Non-cross-linked hyaluronic acid | |
|---|---|---|---|---|---|---|
|  | Content | Content ratio | Content | Content ratio | Content | Content ratio |
| Preparation Example 1-1 | 10 | 1 | 10 | 1 | 2 | 0.2 |
| Preparation Example 1-2 | 10 | 1 | 10 | 1 | 4 | 0.4 |
| Preparation Example 1-3 | 10 | 1 | 20 | 2 | 2 | 0.2 |
| Preparation Example 1-4 | 10 | 1 | 20 | 2 | 4 | 0.4 |
| Comparative Preparation Example 1-5 | 10 | 1 | 30 | 3 | 2 | 0.2 |
| Comparative Preparation Example 1-6 | 10 | 1 | 30 | 3 | 4 | 0.4 |
| Comparative Preparation Example 1-7 | 10 | 1 | 40 | 4 | 2 | 0.2 |
| Comparative Preparation Example 1-8 | 10 | 1 | 40 | 4 | 4 | 0.4 |
| Comparative Preparation Example 1-9 | 10 | 1 | 50 | 5 | 2 | 0.2 |
| Comparative Preparation Example 1-10 | 10 | 1 | 50 | 5 | 4 | 0.4 |

(2) Measurement of Properties

Measurement results of viscosity, extrusion force, and viscoelasticity of each of the hyaluronic acid compositions according to Preparation Examples 1-1 to 1-4 and Comparative Preparation Examples 1-5 to 1-10 are shown in the following Tables 5 and 6.

TABLE 5

| | First cross-linked hyaluronic acid particle | Second cross-linked hyaluronic acid particle | Non-cross-linked hyaluronic acid | Viscosity (cP) | Extrusion force (N) |
|---|---|---|---|---|---|
| Preparation Example 1-1 | 1 | 1 | 0.2 | 75451 | 20.67 |
| Preparation Example 1-2 | 1 | 1 | 0.4 | 62641 | 19.36 |
| Preparation Example 1-3 | 1 | 2 | 0.2 | 82331 | 29.16 |
| Preparation Example 1-4 | 1 | 2 | 0.4 | 89419 | 23.08 |
| Comparative Preparation Example 1-5 | 1 | 3 | 0.2 | 101965 | 32.02 |
| Comparative Preparation Example 1-6 | 1 | 3 | 0.4 | 100554 | 26.31 |
| Comparative Preparation Example 1-7 | 1 | 4 | 0.2 | 112968 | 35.60 |
| Comparative Preparation Example 1-8 | 1 | 4 | 0.4 | 106860 | 27.82 |
| Comparative Preparation Example 1-9 | 1 | 5 | 0.2 | 111545 | 41.59 |
| Comparative Preparation Example 1-10 | 1 | 5 | 0.4 | 107103 | 31.04 |

As shown in Table 5, the compositions according to Comparative Preparation Examples 1-5 to 1-10, in which a weight ratio of second cross-linked hyaluronic acid to first cross-linked hyaluronic acid was 3 to 5:1, exhibited a high viscosity of 100,000 cP or more, and thus are not appropriate for use as a filler composition.

TABLE 6

| | First cross-linked hyaluronic acid particle | Second cross-linked hyaluronic acid particle | Non-cross-linked hyaluronic acid | Elasticity | G' | G" | Phase angle |
|---|---|---|---|---|---|---|---|
| Preparation Example 1-1 | 1 | 1 | 0.2 | 84.46 | 761.5 | 140.1 | 10.42 |
| Preparation Example 1-2 | 1 | 1 | 0.4 | 76.79 | 523.7 | 158.3 | 16.82 |
| Preparation Example 1-3 | 1 | 2 | 0.2 | 86.75 | 1011 | 154.4 | 8.69 |
| Preparation Example 1-4 | 1 | 2 | 0.4 | 85.25 | 888.8 | 153.8 | 9.81 |
| Comparative Preparation Example 1-5 | 1 | 3 | 0.2 | 89.65 | 1252 | 144.6 | 6.59 |
| Comparative Preparation Example 1-6 | 1 | 3 | 0.4 | 87.11 | 1045 | 154.7 | 8.42 |
| Comparative Preparation Example 1-7 | 1 | 4 | 0.2 | 90.72 | 1371 | 140.3 | 5.84 |
| Comparative Preparation Example 1-8 | 1 | 4 | 0.4 | 88.78 | 1238 | 156.5 | 7.21 |
| Comparative Preparation Example 1-9 | 1 | 5 | 0.2 | 90.61 | 1465 | 151.8 | 5.91 |
| Comparative Preparation Example 1-10 | 1 | 5 | 0.4 | 88.70 | 1366 | 174 | 7.26 |

In addition, as shown in Table 6, some of the compositions according to Comparative Preparation Examples 1-5 to 1-10, in which a weight ratio of second cross-linked hyaluronic acid to first cross-linked hyaluronic acid was 3 to 5:1, exhibited low phase angles of less than 7.

Although the compositions according to Comparative Preparation Examples 1-6, 1-8, and 1-10 exhibited phase angles of 7 or more, they had high viscosities as shown in Table 5, and thus are not appropriate for use as a filler composition.

That is, when first cross-linked hyaluronic acid and second cross-linked hyaluronic acid are included in a weight ratio of 1:0.5 or more to 2.5 or less, a hyaluronic acid composition having excellent properties (such as viscosity, extrusion force, and viscoelasticity) can be prepared.

Example 3. Evaluation of Properties of Hyaluronic Acid Composition According to Content of Non-Cross-Linked Hyaluronic Acid (1) Preparation of Hyaluronic Acid Composition (Preparation Examples 1-1, 1-2, and 1-11 to 1-13)

Hyaluronic acid compositions were prepared using first cross-linked hyaluronic acid particles, second cross-linked hyaluronic acid particles, and non-cross-linked hyaluronic acid in contents (g) and content ratios as shown in the following Table 7.

TABLE 7

| | First cross-linked hyaluronic acid particle | | Second cross-linked hyaluronic acid particle | | Non-cross-linked hyaluronic acid | |
|---|---|---|---|---|---|---|
| | Content | Content ratio | Content | Content ratio | Content | Content ratio |
| Preparation Example 1-1 | 10 | 1 | 10 | 1 | 2 | 0.2 |
| Preparation Example 1-2 | 10 | 1 | 10 | 1 | 4 | 0.4 |
| Preparation Example 1-11 | 10 | 1 | 10 | 1 | 6 | 0.6 |
| Preparation Example 1-12 | 10 | 1 | 10 | 1 | 8 | 0.8 |
| Preparation Example 1-13 | 10 | 1 | 10 | 1 | 10 | 1.0 |

(2) Measurement of Properties

Measurement results of viscosity, extrusion force, and viscoelasticity of each of the hyaluronic acid compositions according to Preparation Examples 1-1, 1-2, and 1-11 to 1-13 are shown in the following Tables 8 and 9.

TABLE 8

| | First cross-linked hyaluronic acid particle | Second cross-linked hyaluronic acid particle | Non-cross-linked hyaluronic acid | Viscosity (cP) | Extrusion force (N) |
|---|---|---|---|---|---|
| Preparation Example 1-1 | 1 | 1 | 0.2 | 75451 | 20.67 |
| Preparation Example 1-2 | 1 | 1 | 0.4 | 62641 | 19.36 |
| Preparation Example 1-11 | 1 | 1 | 0.6 | 53402 | 16.42 |
| Preparation Example 1-12 | 1 | 1 | 0.8 | 50216 | 18.01 |
| Preparation Example 1-13 | 1 | 1 | 1.0 | 45046 | 16.06 |

As shown in Table 8, the viscosities of the hyaluronic acid compositions according to Preparation Examples 1-1, 1-2, and 1-11 to 1-13 satisfied the viscosity range of 45,000 to 90,000 cP according to the present invention. Particularly, the compositions including non-cross-linked hyaluronic acid in weight ratios of 0.2 or 0.4 exhibited viscosities of 60,000 to 80,000 cP, which are highly appropriate for a filler for dermal injection.

TABLE 9

| | First cross-linked hyaluronic acid particle | Second cross-linked hyaluronic acid particle | Non-cross-linked hyaluronic acid | Elasticity | G' | G" | Phase angle |
|---|---|---|---|---|---|---|---|
| Preparation Example 1-1 | 1 | 1 | 0.2 | 84.46 | 761.5 | 140.1 | 10.42 |
| Preparation Example 1-2 | 1 | 1 | 0.4 | 76.79 | 523.7 | 158.3 | 16.82 |
| Preparation Example 1-11 | 1 | 1 | 0.6 | 74.89 | 412.1 | 138.2 | 18.54 |
| Preparation Example 1-12 | 1 | 1 | 0.8 | 72.18 | 332.7 | 128.2 | 21.07 |
| Preparation Example 1-13 | 1 | 1 | 1.0 | 66.95 | 266.4 | 131.5 | 26.27 |

In addition, as shown in Table 9, the hyaluronic acid compositions according to Preparation Examples 1-1, 1-2, and 1-11 to 1-13 exhibited elasticities of 65 to 90 and phase angles of 8 to 30, both of which satisfied the ranges according to the present invention. Particularly, the compositions including non-cross-linked hyaluronic acid in weight ratios of 0.2 or 0.4 exhibited elasticities of 75 to 85 and phase angles of 10 to 20, indicating that they have highly appropriate viscoelasticity for a filler for dermal injection.

That is, when first cross-linked hyaluronic acid and second cross-linked hyaluronic acid are included in a weight ratio of 1:0.5 or more to less than 1.5, and first cross-linked hyaluronic acid and non-cross-linked hyaluronic acid are included in a weight ratio of 1:0.1 or more to less than 0.5, a composition is appropriate for use for dermal injection.

A composition for dermal injection according to the present invention satisfies viscosity, extrusion force, and viscoelasticity conditions for dermal injection, and an extrusion force deviation is low so that the user does not feel fatigue when the composition is injected into the dermal thereof.

Also, the composition is excellent in viscoelasticity and tissue restoring ability, is maintained for a long period of time, allows rapid recovery because an initial swelling degree is low, and also is excellent in safety and stability in the body.

What is claimed is:

1. A composition for dermal injection, comprising first cross-linked hyaluronic acid particles, second cross-linked hyaluronic acid particles having different particle diameters from the first cross-linked hyaluronic acid particles, and non-cross-linked hyaluronic acid, wherein the first cross-linked hyaluronic acid particles and the second cross-linked hyaluronic acid particles are included in a weight ratio of 1:0.5 or more to less than 2.5, and the first cross-linked hyaluronic acid particles and the non-cross-linked hyaluronic acid are included in a weight ratio of 1:0.1 or more to 1.2 or less wherein the first cross-linked hyaluronic acid particles have an average particle diameter of 10 to 250 μm, and wherein the second cross-linked hyaluronic acid particles have an average particle diameter of 700 to 1,500 μm.

2. The composition of claim 1, wherein the first cross-linked hyaluronic acid particles and the second cross-linked hyaluronic acid particles are included in a weight ratio of 1:0.5 or more to less than 1.5, and the first cross-linked hyaluronic acid particles and the non-cross-linked hyaluronic acid are included in a weight ratio of 1:0.1 or more to less than 0.5.

3. The composition of claim 1, wherein the first cross-linked hyaluronic acid particle, the second cross-linked hyaluronic acid particle, or the non-cross-linked hyaluronic acid has a molecular weight of 1,000,000 to 1,500,000 Da.

4. The composition of claim 1, wherein the first cross-linked hyaluronic acid particle or the second cross-linked hyaluronic acid particle has a degree of crosslinking of 10 to 20 mol %.

5. The composition of claim 1, wherein the first cross-linked hyaluronic acid particles, the second cross-linked hyaluronic acid particles, and the non-cross-linked hyaluronic acid are included at 1 to 10 parts by weight with respect to 100 parts by weight of the entire composition.

6. The composition of claim 1, further comprising epidermal growth factor (EGF).

7. The composition of claim 6, wherein the epidermal growth factor (EGF) is included at 0.0001 to 0.002 part by weight with respect to 100 parts by weight of the entire composition.

8. The composition of claim 1, further comprising an anesthetic component.

9. The composition of claim 8, wherein the anesthetic component is included at 0.1 to 1 part by weight with respect to 100 parts by weight of the composition.

10. The composition of claim 1, wherein the composition for dermal injection has the following physicochemical properties:
   (a) no bubbles in appearance, colorlessness, and transparency,
   (b) a pH of 7±1,
   (c) a viscosity of 40,000 to 90,000 cP,
   (d) an average osmotic pressure of 0.325 osmol/kg±10%,
   (e) an extrusion force of 30 N or less,
   (f) an elasticity of 65 to 90%, and
   (g) a phase angle of 8 to 30°.

11. The composition of claim 10, wherein the composition for dermal injection has a viscosity of 60,000 to 80,000 cP.

12. The composition of claim 10, wherein the composition for dermal injection has an extrusion force of 25 N or less.

13. The composition of claim 10, wherein the composition for dermal injection has an elasticity of 75 to 85% and a phase angle of 10 to 20°.

* * * * *